:(12) United States Patent
Sakamoto et al.

(10) Patent No.: US 6,835,559 B2
(45) Date of Patent: Dec. 28, 2004

(54) PROCESS FOR THE PRODUCTION OF OPTICALLY ACTIVE β-AMINO ALCOHOLS

(75) Inventors: Keiji Sakamoto, Takaoka (JP); Shinji Kita, Takaoka (JP); Kazuya Tsuzaki, Takaoka (JP); Tadanori Morikawa, Takaoka (JP); Sakayu Shimizu, Kyoto (JP); Michihiko Kataoka, Kyoto (JP)

(73) Assignee: Daiichi Fine Chemical Co., Ltd., Toyama (JP)

( * ) Notice: Subject to any disclaimer, the term of this patent is extended or adjusted under 35 U.S.C. 154(b) by 31 days.

(21) Appl. No.: 10/240,056

(22) PCT Filed: Mar. 2, 2001

(86) PCT No.: PCT/JP01/01628

§ 371 (c)(1),
(2), (4) Date: Jan. 22, 2003

(87) PCT Pub. No.: WO01/73100

PCT Pub. Date: Oct. 4, 2001

(65) Prior Publication Data

US 2004/0091981 A1 May 13, 2004

(30) Foreign Application Priority Data

Mar. 28, 2000 (JP) .......................................... 2000-89182

(51) Int. Cl.⁷ .............................................. C12P 13/00
(52) U.S. Cl. ...................... 435/128; 435/169; 435/170; 435/280; 435/822; 435/865; 435/877; 435/911; 435/914; 435/917; 435/918
(58) Field of Search ................................ 435/128, 169, 435/170, 280

(56) References Cited

U.S. PATENT DOCUMENTS 4,237,304 A    12/1980  Dowd et al. ................. 548/239
4,879,233 A    11/1989  Charney ...................... 435/254

FOREIGN PATENT DOCUMENTS

EP    0654534A2 A3    5/1995
EP    0779366 A1      6/1997
JP    10-248591       9/1998
WO    WO98/12155      3/1998

OTHER PUBLICATIONS

"Enantioselective Synthesis of Both Enantiomers of Cathinone via the Microbiological Reduction of 2–Azido–1–Phenyl–1–Propanone" as published in: Journal Organic Chemistry 1994, vol. 59, pp. 8288–8291 (4 pages) Authors: Pascale Besse, Henri Veschambre, Michael Dickman and Robert Chenevert.
"Enantioselective Synthesis of Optically Active B–Aminoalcohols via Asymmetric Reduction" as published in: Tetrahedron Asymmetry, 1992, vol. 3, No. 3, pp. 341–342 (2 pages) (published in Great Britain) Authors: Byung Tae Cho and Yu Sung Chun.

"Asymmetric Amplifying Phenomena in Enantioselective Addition of Diethylzine to Benzaldehyde" as published in: Journal American Chemical Society,1988, vol. 110, pp. 7877–7878 (2 pages) Authors: N. Oguni, Y. Matsuda, and T. Kaneko.
"Occurrence of an Inducible NADP –Dependent D–Phenylserine Dehydrogenase in Pseudomonas Syringae NK–15 Isolated from Soil" Authors: Kanoktip Packdibamrung, Haruo Misono, Shinji Nagata and Susumu Nagasaki of the Laboratory of Applied Microbiology, Department of Bioresources Science, Kochi University, Nankoku, Kochi 783, Japan, Received May 24, 1993, 4 pages.
"Biological Method for Preparation of Both Pure Enantiomers of a Chiral Compound: The Case of 2–Amino–1–Phenylethanol" as published in Chemistry Express, vol. 4, No. 9, 1989 (6 pages) Authors: Yoshimitsu Yamazaki, Kazuya Mochizuki and Kuniaki Hosono.
Patent Abstracts of Japan publication No. 10–248591 published Sep. 22, 1998.
"An Enantioselective Synthesis of (IS, 2S)–Pseudoephedrine" as published in Tetrahedron Letters 41 (2000) pp. 953–954 (2 pages) Authors: G. Vidyasagar Reddy, G. Venkat Rao, V. Sreevani and D.S. Iyengar.
Patentschrift Nr. 11332filed Oct. 18, 1953, published Mar. 12, 1956 (3 pages) and Partial English Translation (1 page).
Patentschrift Nr. 13683, filed Jan. 19, 1956, published Aug. 27, 1957 (3 pages) and partial English translation (1 page).

Primary Examiner—Herbert J. Lilling
(74) Attorney, Agent, or Firm—Osha & May L.L.P.

(57) ABSTRACT

A process for producing an optical active β-amino alcohol, the method comprising the step of allowing at least one microorganism selected from the group consisting of microorganisms belonging to the genus Morganella and others, to act on an enantiomeric mixture of an α-aminoketone or a salt thereof having the general formula (I):

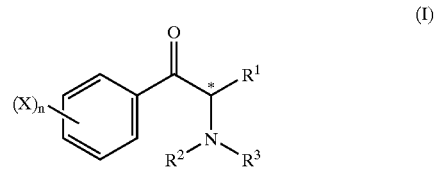

(I)

to produce an optical active β-amino alcohol with the desired optical activity having the general formula (II) described below in a high yield as well as in a highly selective manner:

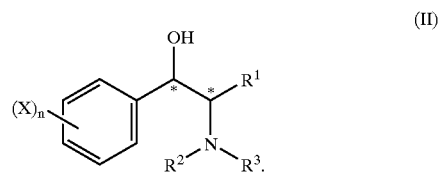

(II)

7 Claims, 1 Drawing Sheet

(1S,2S)CONFIGURATION (1S,2S)-(+)-PSEUDOEPHEDRINE (1R,2R)CONFIGURATION (1R,2R)-(-)-PSEUDOEPHEDRINE

PROCESS FOR THE PRODUCTION OF OPTICALLY ACTIVE β-AMINO ALCOHOLS

TECHNICAL FIELD

This invention relates to a process for producing optically active β-amino alcohols. More particularly, it relates to a process for producing optically active β-amino alcohols which are of value as drugs or their intermediates.

BACKGROUND ART

Ephedrines have been used for purposes of perspiration, antipyresis and cough soothing from the olden times, and particularly, d-pseudoephedrine is known to possess anti-inflammatory action. Pharmacological action such as vasoconstriction, blood pressure elevation, or perspiration is known for 1-ephedrine and it is used in therapy as a sympathomimetic agent. 1-Ephedrine is also used in the treatment of bronchial asthma. Specifically, processes for the production of optically active β-amino alcohols, including optically active ephedrines, are useful in the manufacture of drugs and their intermediates; thus, there is a need for efficient production processes.

In the conventional process for producing a β-amino alcohol with the desired optical activity, there was used a process by which a racemic β-amino alcohol is obtained and then a specific optically active form is produced by optical resolution or asymmetric synthesis among others.

However, since the racemic β-amino alcohol has two asymmetric carbons within its molecule, complicated steps had to be followed to obtain the specific optically active form. For example, according to Ger. (East) 13683 (Aug. 27, 1957), optically active phenylacetylcarbinol was produced from benzaldehyde by fermentation utilizing yeast and erythro-1-2-methylamino-1-phenyl-1-propanol (i.e., 1-ephedrine) could be produced by reductively condensing methylamine to the optically active phenylacetylcarbinol.

To obtain pseudoephedrine, the production is possible as described in U.S. Pat. No. 4,237,304: an oxazoline is formed from 1-ephedrine produced by the method described in Ger. (East) 13683 (Aug. 27, 1957), using acetic anhydride, and then the oxazoline is hydrolyzed through inversion to the threo form (i.e., d-pseudoephedrine).

As stated above, to produce pseudoephedrine with the desired optical activity from 2-methylamino-1-phenyl-1-propanone, steps are necessary such that ephedrine in the optical active erythro form is once produced and then it is inverted to the threo form. Hence, there arise problems that the number of steps grows and leads to complication and that the yields lower.

Furthermore, in the production of the pseudoephedrine while a substantial amount of diastereomers is produced as byproducts during the reduction of the starting ketone, the recovery of the diastereomers for their use as raw material is difficult, which is economically disadvantageous.

In addition, according to the method as described in the publication of JP, 8-98697, A, it is possible to produce an optically active 2-amino-1-phenylethanol derivative from a 2-amino-1-phenylethanol compound having one asymmetric carbon atom within its molecule through the use of a specific microorganism. The present state of art is, however, that there has been no efficient process for producing β-amino alcohol having two asymmetric carbon atoms.

DISCLOSURE OF THE INVENTION

This invention has been made in view of the above-indicated circumstances and it aims at producing a β-amino alcohol having the desired optical activity from an enantiomeric mixture of an α-aminoketone compound or its salt in a high yield as well as in a highly selective manner with a simple process while sufficiently preventing the generation of diastereomeric byproducts.

The present inventors repeated studies diligently to solve the above-stated problems; consequently, it was discovered that by utilizing specific microorganisms only one enantiomer of the enantiomeric mixture of an α-aminoketone compound or its salt could be reduced to produce the only desired kind among the corresponding four kinds of β-amino alcohols in a high yield as well as in a highly selective manner. This led to the completion of the present invention.

Specifically, the process for producing an optically active β-amino alcohol according to this invention comprises allowing at least one microorganism selected from the group consisting of microorganisms belonging to the genus *Morganella*, the genus *Microbacterium*, the genus *Sphingobacterium*, the genus *Nocardicides*, the genus *Mucor*, the genus *Absidia*, the genus *Aspergillus*, the genus *Penicillium*, the genus *Grifola*, the genus *Eurotium*, the genus *Ganoderma*, the genus *Hypocrea*, the genus *Helicostylum*, the genus *Verticillium*, the genus *Fusarium*, the genus *Tritirachium*, the genus *Mortierella*, the genus *Armillariella*, the genus *Cylindrocarpon*, the genus *Kiebsiella*, the genus *Aureobacterium*, the genus *Xanthomonas*, the genus *Pseudomonas*, the genus *Mycobacterium*, the genus *Sporobolomyces*, the genus *Sporidiobolus*, the genus *Amycolatopsis*, the genus *Coprinus*, the genus *Serratia*, the genus *Rhodococuss* and the genus *Rhodotorula* to act on an enantiomeric mixture of an α-aminoketone or a salt thereof having the general formula (1):

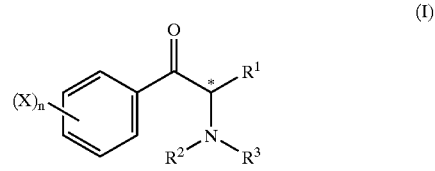

(I)

wherein X may be the same or different and represents at least one member selected from the group consisting of a halogen atom, lower alkyl, hydroxyl optionally protected with a protecting group, nitro and sulfonyl; n represents an integer of from 0 to 3; $R^1$ represents lower alkyl; $R^2$ and $R^3$ may be the same or different and represent at least one member selected from the group consisting of a hydrogen atom and lower alkyl; and "*" represents an asymmetric carbon, to produce an optically active β-amino alcohol compound with the desired optical activity having the general formula (II):

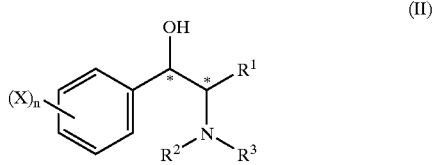

wherein X, n, $R^1$, $R^2$, $R^3$ and "*" are as previously defined.

The microorganism according to this invention is preferably at least one microorganism selected from the group consisting of microorganisms belonging to *Morganella morganii, Microbacterium arborescens, Sphingobacterium multivorum, Nocardioides simplex, Mucor ambiguus, Mucor javanicus, Mucor fragilis, Absidia lichtheimi, Aspergillus awamori, Aspergillus niger, Aspergillus oryzae, Aspergillus candidus, Aspergillus oryzae* var. *oryzae, Aspergillus foetidus* var. *acidus, Penicillium oxalicum, Grifola frondosa, Eurotium repens, Ganoderma lucidum, Hypocrea gelatinosa, Helicostylum nigricans, Verticillium fungicola* var. *fungicola, Fusarium roseum, Tritirachium oryzae, Mortierella isabellina, Armillariella mellea, Cylindrocarpon sclerotigenum, Klebsiella pneumoniae, Aureobacterium esteraromaticum, Xanthomonas* sp., *Pseudomonas putida, Mycobacterium smegmatis, Mycobacterium diernhoferi, Mycobacterium vaccae, Mycobacterium phlei, Mycobacterium fortuitum, Mycobacterium chlorophenolicum, Sporobolomyces salmonicolor, Sporobolomyces coralliformis, Sporidiobolus johnsonii, Amycolatopsis alba, Amycolatopsis azurea, Amycolatopsis coloradensis, Amycolatopsis orientalis lurida, Amycolatopsis orientalis orientalis, Coprinus rhizophorus, Serratia marcescens, Rhodococcus erythropolis, Rhodococcus rhodochrous* and *Rhodotorula aurantiaca*.

In this invention the microorganism is preferably at least one microorganism selected from the group consisting of microorganisms belonging to the genus *Morganella*, the genus *Microbacterium*, the genus *Sphingobacterium*, the genus *Nocardioides*, the genus *Mucor*, the genus *Absidia*, the genus *Aspergillus*, the genus *Penicillium*, the genus *Grifola*, the genus *Eurotium*, the genus *Ganoderma*, the genus *Hypocrea*, the genus *Helicostylum*, the genus *Verticillium*, the genus *Fusarium*, the genus *Tritirachium*, the genus *Mortierella*, the genus *Armillariella*, the genus *Cylindrocarpon*, the genus *Klebsiella*, the genus *Aureobacterium*, the genus *Xanthomonas*, the genus *Pseudomonas*, the genus *Mycobacterium*, the genus *Sporobolomyces*, the genus *Sporidiobolus* and the genus *Rhodococuss*. More specifically, it is preferably a microorganism selected from the group consisting of microorganisms belonging to *Morganella morganii, Microbacterium arborescens, Sphingobacterium multivorum, Nocardioides simplex, Mucor ambiguus, Mucor javanicus, Mucor fragilis, Absidia lichtheimi, Aspergillus awamori, Aspergillus niger, Aspergillus oryzae, Aspergillus candidus, Aspergillus oryzae* var. *oryzae, Aspergillus foetidus* var. *acidus, Penicillium oxalicum, Grifola frondosa, Eurotium repens, Ganoderma lucidum, Hypocrea gelatinosa, Helicostylum nigricans, Verticillium fungicola* var. *fungicola, Fusarium roseum, Tritirachium, oryzae, Mortierella isabellina, Armillariella mellea, Cylindrocarpon sclerotigenum, Klebsiella pneumoniae, Aureobacterium esteraromaticum, Xanthomonas* sp., *Pseudomonas putida, Mycobacterium smegmatis, Mycobacterium diernhoferi, Mycobacterium vaccae, Mycobacterium phlei, Mycobacterium fortuitum, Mycobacterium chlorophenolicum, Sporobolomyces salmonicolor, Sporobolomyces coralliformis, Sporidiobolus johnsonii, Rhodococus erythropolis* and *Rhodococcus rhodochrous*. By utilizing such microorganisms, (1S,2S)-amino alcohols tend to be obtained in simple processes as the optically active β-amino alcohols represented by the general formula (II) in high yields as well as in a highly selective manner.

Further, the microorganism is preferably at least one microorganism selected from the group consisting of microorganisms belonging to the genus *Amycolaptopsis*, the genus *Coprinus*, the genus *Serratia*, the genus *Rhodococuss* and the genus *Rhodotorula*. More specifically, it is preferably a microorganism selected from the group consisting of microorganisms belonging to *Amycolatopsis alba, Amycolatopsis azurea, Amycolatopsis coloradensis, Amycolatopsis orientalis lurida, Amycolatopsis orientalis orientalis, Coprinus rhizophorus, Serratia marcescens, Rhodococcus erythropolis, Rhodococcus rhodochrous* and *Rhodotorula aurantiaca*. By utilizing such microorganisms, (1R,2R)-amino alcohols tend to be obtained in simple processes as the optically active β-amino alcohols represented by the general formula (II) in high yields as well as in a highly selective manner.

Still further, in this invention the microorganism may be cultured in a medium to which there has been added an activity inducer having the general formula (III):

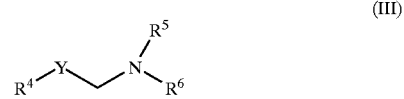

wherein $R^4$ represents lower alkyl; $R^5$ and $R^6$ may be the same or different and each represents a hydrogen atom, lower alkyl or acyl; and Y represents C=O or CH—OH. The mediation of such an activity inducer renders the production of an optically active β-amino alcohol more efficient.

BRIEF DESCRIPTION OF THE DRAWINGS

FIG. 1A shows a β-amino alcohol with the (1S,2S) configuration obtained according to this invention. FIG. 1B shows (1S,2S)-(+)-pseudoephedrine obtained according to the invention. FIG. 1C shows a β-amino alcohol with the (1R,2R) configuration obtained according to the invention. FIG. 1D shows (1R,2R)-(−)-pseudoephedrine obtained according to this invention.

BEST MODE FOR CARRYING OUT THE INVENTION

Figure 1A:
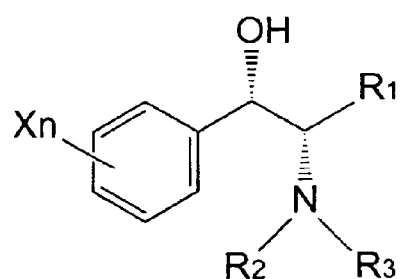
FIGS. 1A through 1D are representations showing the structures of the optically active β-amino alcohols described below, including their absolute configurations.
Figure 1B:
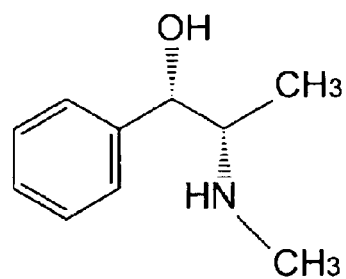
Figure 1C:
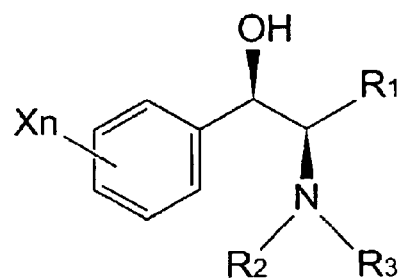
Figure 1D:
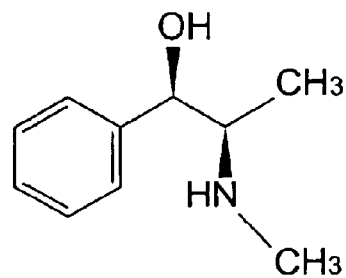

The preferred embodiments of this invention will be described in detail hereafter.

The process for producing an optically active β-amino alcohol according to this invention comprises allowing at least one microorganism selected from the group consisting of microorganisms belonging to the genus *Morganella*, the genus *Microbacterium*, the genus *Sphingobacterium*, the genus *Nocardioides*, the genus *Mucor*, the genus *Absidia*, the genus *Aspergillus*, the genus *Penicillium*, the genus *Grifola*, the genus *Eurotium*, the genus *Ganoderma*, the genus *Hypocrea*, the genus *Helicostylum*, the genus *Verticillium*, the genus *Fusarium*, the genus *Tritirachium*, the genus *Mortierella*, the genus *Armillanella*, the genus *Cylindrocarpon*, the genus *Kiebsiella*, the genus *Aureobacterium*, the genus *Xanthomonas*, the genus *Pseudomonas*, the genus *Mycobacterium*, the genus *Sporobolomyces*, the genus *Sporidiobolus*, the genus *Amycolatopsis*, the genus *Coprinus*, the genus *Serratia*, the genus *Rhodococuss*, and the genus *Rhodotorula* to act on an enantiomeric mixture of an α-amino ketone compound or a salt thereof having the general formula (I):

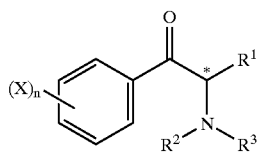

(I)

wherein X may be the same or different and represents at least one member selected from the group consisting of a halogen atom, lower alkyl, hydroxyl optionally protected with a protecting group, nitro and sulfonyl; n represents an integer of from 0 to 3; $R^1$ represents lower alkyl; $R^2$ and $R^3$ may be the same or different and represent at least one member selected from the group consisting of a hydrogen atom and lower alkyl; and "*" represents an asymmetric carbon, to produce an optically active β-amino alcohol compound with the desired optical activity having the general formula (II):

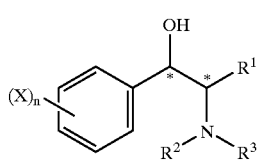

(II)

wherein X, n, $R^1$, $R^2$, $R^3$ and "*" are as previously defined.

The starting material used in the process for producing an optically active β-amino alcohol according to this invention is an enantiomeric mixture of an α-aminoketone compound or a salt thereof having the general formula (I) wherein X may be the same or different and represents at least one member selected from the group consisting of a halogen atom, lower alkyl, hydroxyl optionally protected with a protecting group, nitro and sulfonyl; n represents an integer of from 0 to 3; $R^1$ represents lower alkyl; $R^2$ and $R^3$ may be the same or different and represent at least one member selected from the group consisting of a hydrogen atom and lower alkyl; and "*" represents an asymmetric carbon.

The substituent group X contained in the α-amino ketone will be described in the following: the halogen atoms include a fluorine atom, a chlorine atom, a bromine atom and an iodine atom.

The lower alkyl groups are preferably alkyls of from one to six carbons and include methyl, ethyl, propyl, isopropyl, butyl, isobutyl, s-butyl, t-butyl, pentyl, isopentyl, hexyl, and the like. These may adopt either of straight chain and branched structures and may have as a substituent, a halogen atom such as fluorine or chlorine, hydroxyl, alkyl, amino, or alkoxy.

For the protecting group of the hydroxyl optionally protected with a protecting group, there are mentioned, among others, the one that can be removed upon treatment with water, the one that can be removed by hydrogenation, the one that can be removed by a Lewis acid catalyst or thiourea. The protecting groups include acyl optionally having a substituent, silyl optionally having a substituent, alkoxyalkyl, lower alkyl optionally having a substituent, benzyl, p-methoxybenzyl, 2,2,2-trichloroethoxycarbonyl, allyloxycarbonyl, trityl and the like.

The acyl groups include acetyl, chloroacetyl, dichloroacetyl, pivaloyl, benzoyl, p-nitrobenzoyl, and the like; they may also have a substituent such as hydroxyl, alkyl, alkoxy, nitro, a halogen atom, or the like. The silyl groups include trimethylsilyl, t-butyldimethylsilyl, triarylsilyl, and the like; they may also have a substituent such as alkyl, aryl, hydroxyl, alkoxy, nitro, a halogen atom, or the like. The alkyl groups include methoxymethyl, 2-methoxyethoxymethyl and the like. The lower alkyl groups include alkyls of from one to six carbons: there are mentioned methyl, ethyl, propyl, isopropyl, butyl, isobutyl, s-butyl, t-butyl, pentyl, isopentyl, hexyl, and the like. These may adopt either of straight chain and branched structures and may have a substituent such as a halogen atom (including fluorine and chlorine), hydroxyl, alkyl, amino, or alkoxy.

The X may be nitro or sulfonyl, and specifically, methylsulfonyl is mentioned among others.

In addition, the number n of X is an integer of from 0 to 3, preferably 0.

$R^1$ in the general formula (I) represents lower alkyl. Such lower alkyls are preferably alkyls of from one to six carbons: there are mentioned methyl, ethyl, propyl, isopropyl, butyl, isobutyl, s-butyl, t-butyl, pentyl, isopentyl, hexyl, and the like. These may adopt either of straight chain and branched structures.

$R^2$ and $R^3$ represent a hydrogen atom or lower alkyl. The lower alkyls include alkyls of from one to six carbons: there are mentioned methyl, ethyl, propyl, isopropyl, butyl, isobutyl, s-butyl, t-butyl, pentyl, isopentyl, hexyl, and the like. These may adopt either of straight chain and branched structures.

The salts of the α-aminoketone compound include the salts of inorganic acids such as hydrochloride, sulfate, nitrate, phosphate, and carbonate and the salts of organic acids such as acetate and citrate.

The α-aminoketone can readily be synthesized by halogenating the α-carbon of the corresponding 1-phenyl ketone derivative (e.g., bromination) and substituting the halogen such as bromo for amine (Ger. (East) 11, 332, Mar. 12, 1956).

The microorganism according to this invention is that which act on the enantiomeric mixture of the a α-minoketone having the general formula (I) or a salt thereof. Such microorganism is one selected from the group consisting of microorganisms belonging to the genus *Morganella*, the genus *Microbacterium*, the genus

*Sphingobacterium*, the genus *Nocardioides*, the genus *Mucor*, the genus *Absidia*, the genus *Aspergillus*, the genus *Penicillium*, the genus *Grifola*, the genus *Eurotium*, the genus *Ganoderma*, the genus *Hypocrea*, the genus *Helicostylum*, the genus *Verticillium*, the genus *Fusarium*, the genus *Tritirachium*, the genus *Mortierella*, the genus *Armillariella*, the genus *Cylindrocarpon*, the genus *Klebsiella*, the genus *Aureobacterium*, the genus *Xanthomonas*, the genus *Pseudomonas*, the genus *Mycobacterium*, the genus *Sporobolomyces*, the genus *Sporidiobolus*, the genus Amycolatopsis, the genus *Coprinus*, the genus *Serratia*, the genus *Rhodococuss* and the genus *Rhodotorula*. Specifically, the preferred ones include *Morganella morganii* IFO 3848, *Microbacterium arborescens* IFO 3750, *Sphingobacterium multivorum* IFO 14983, *Nocardioides simplex* IFO 12069, *Mucor ambiguus* IFO 6742, *Mucor javanicus* IFO 4570, *Mucor fragilis* IFO 6449, *Absidia lichtheimi* IFO 4009, *Aspergillus awamori* IFO 4033, *Aspergillus niger* IFO 4416, *Aspergillus oryzae* IFO 4177, *Aspergillus oryzae* IAM 2630, *Aspergillus candidus* IFO 5468, *Aspergillus oryzae* var. *oryzae* IFO 6215, *Aspergillus foetidus* var. *acidus* IFO 4121, *Penicillium oxalicum* IFO 5748, *Grifola frondosa* IFO 30522, *Eurotium repens* IFO 4884, *Ganoderma lucidum* IFO 8346, *Hypocrea gelatinosa* IFO 9165, *Helicostylum nigricans* IFO 8091, *Verticillium fungicola* var. *fungicola* IFO 6624, *Fusarium roseum* IFO 7189, *Tritirachium, oryzae* IFO 7544, *Mortierella isabellina* IFO 8308, *Armillariella mellea* IFO 31616, *Cylindrocarpon sclerotigenum* IFO 31855, *Klebsiella pneumoniae* IFO 3319, *Aureobacterium esteraromaticum* IFO 3751, *Xanthomonas* sp. IFO 3084, *Pseudomonas putida* IFO 14796, *Mycobacterium smegmatis* IAM 12065, *Mycobacterium diernhoferi*, IFO 14797, *Mycobacterium vaccae* IFO 14118, *Mycobacterium phlei* IFO 13160, *Mycobacterium fortuitum* IFO 13159, *Mycobacterium chlorophenolicum* IFO 15527, *Sporobolomyces salmonicolor* IFO 1038, *Sporobolomyces coralliformis* IFO 1032, *Sporidiobolus johnsonii* IFO 6903, *Amycolatopsis alba* IFO 15602, *Amycolatopsis azurea* IFO 14573, *Amycolatopsis coloradensis* IFO 15804, *Amycolatopsis orientalis lurida* IFO 14500, *Amycolatopsis orientalis orientalis* IFO 12360, IFO 12362, IFO 12806, *Coprinus rhizophorus* IFO 30197, *Serratia marcescens* IFO 3736, *Rhodococcus erythropolis* IFO 12540, *Rhodococcus erythropolis* MAK-34, *Rhodococcus rhodochrous* IFO 15564, *Rhodococcus rhodochrous* IAM 12126, *Rhodotorula aurantiaca* IFO 0951, and the like.

Such microorganisms according to this invention permit the production of the corresponding optically active β-amino alcohol compounds having the general formula (II), said compound possessing the desired optical activity.

In the general formula (II), X, n, $R^1$, $R^2$, $R^3$ and*are the same as those in the general formula (I). Further, the β-amino alcohols having the desired optical activity include (1S,2S)-amino alcohol, (1S,2R)-amino alcohol, (1R,2S)-amino alcohol and (1R,2R)-amino alcohol.

In this invention the microorganism is preferably at least one selected from the group consisting of microorganisms belonging to the genus *Morganella* genus, the genus *Microbacterium*, the genus *Sphingobacterium*, the genus *Nocardioides*, the genus *Mucor*, the genus *Absidia*, the genus *Aspergillus*, the genus *Penicillium*, the genus *Grifola*, the genus *Eurotium*, the genus *Ganoderma*, the genus *Hypocrea*, the genus *Helicostylum*, the genus *Verticillium*, the genus *Fusarium*, the genus *Tritirachium*, the genus *Mortierella*, the genus *Armillariella*, the genus *Cylindrocarpon*, the genus *Klebsiella*, the genus *Aureobacterium*, the genus *Xanthomonas*, the genus *Pseudomonas*, the genus *Mycobacterium*, the genus *Sporobolomyces*, the genus *Sporidiobolus* and the genus *Rhodococuss*. More specifically, preferred is a microorganism selected from the group consisting of microorganisms belonging to *Morganella morganii, Microbacterium arborescens, Sphingobacterium multivorum, Nocardioides simplex, Mucor ambiguus, Mucor javanicus, Mucor fragilis, Absidia lichtheimi, Aspergillus awamori, Aspergillus niger, Aspergillus oryzae, Aspergillus candidus, Aspergillus oryzae* var. *oryzae, Aspergillus foetidus* var. *acidus, Penicillium oxalicum, Grifola frondosa, Eurotium repens, Ganoderma lucidum, Hypocrea gelatinosa, Helicostylum nigricans, Verticillium fungicola* var. *fungicola, Fusarium roseum, Tritirachium, oryzae, Mortierella isabellina, Armillariella mellea, Cylindrocarpon sclerotigenum, Klebsiella pneumoniae, Aureobacterium esteraromaticum,* Xanthomonas sp., *Pseudomonas putida, Mycobacterium smegmatis, Mycobacterium diernhoferi, Mycobacterium vaccae, Mycobacterium phlei, Mycobacterium fortuitum, Mycobacterium chlorophenolicum, Sporobolomyces salmonicolor, Sporobolomyces coralliformis, Sporidiobolus johnsonii, Rhodococcus erythropolis* and *Rhodococcus rhodochrous*. By utilizing such microorganisms, (1S,2S)-amino alcohols tend to be obtained in simple processes as the optically active β-amino alcohols represented by the general formula (II) in high yields as well as in a highly selective manner.

Furthermore, in this invention the microorganism is preferably at least one selected from the group consisting of microorganisms belonging to the genus *Amycolatopsis*, the genus *Coprinus*, the genus *Serratia*, the genus *Rhodococuss* and the genus *Rhodotorula*. More specifically, more preferred is a microorganism selected from the group consisting of microorganisms belonging to *Amycolatopsis alba, Amycolatopsis azurea, Amycolatopsis coloradensis, Amycolatopsis orientalis lurida, Amycolatopsis orientalis orientalis, Coprinus rhizophorus, Serratia marcescens, Rhodococcus erythropolis, Rhodococcus rhodochrous* and *Rhodotorula aurantiaca*. By utilizing such microorganisms, (1R,2R)-amino alcohols tend to be obtained in simple processes as the optically active β-amino alcohols represented by the general formula (II) in high yields as well as in a highly selective manner.

In addition, the microorganisms according to this invention include (1S,2S)-amino alcohol producing bacteria that selectively produce (1S,2S) forms among the optically active β-amino alcohol compounds and (1R,2R)-amino alcohol producing bacteria that selectively produce (1R,2R) forms among the optically active β-amino alcohol compounds.

By allowing the action of the (1S,2S)-amino alcohol producing bacteria, there can be obtained, for example, d-threo-2-methylamino-1-phenylpropanol(d-pseudoephedrine), d-threo-2-dimethylamino-1-phenylpropanol(d-methylpseudoephedrine), (1S,2S)-α-(1-aminoethyl)-benzylalcohol(d-norpseudoephedrine), (1S, 2S)-1-(p-hydroxyphenyl)-2-methylamino-1-propanol, (1S, 2S)-α-(1-aminoethyl)-2,5-dimethoxy-benzylalcohol, (1S, 2S)-1-(m-hydroxyphenyl)-2-amino-1-propanol, (1S,2S)-1-(p-hydroxyphenyl)-2-amino-1-propanol, (1S,2S)-1-phenyl-2-ethylamino-1-propanol, (1S,2S)-1-phenyl-2-amino-1-butanol and (1S,2S)-1-phenyl-2-methylamino-1-butanol. By allowing the action of the (1R,2R)-amino alcohol producing bacteria, there can be obtained, for example, 1-threo-2-methylamino-1-phenylpropanol(1-pseudoephedrine), 1-threo-2-dimethylamino-1-phenylpropanol(1-methylpseudoephedrine), (1R,2R)-α-(1-aminoethyl)-benzylalcohol(1-norpseudoephedrine), (1R,2R)-1-(p-hydroxyphenyl)-2-methylamino-1-propanol, (1R,2R)-α-(1-aminoethyl)-2,5dimethoxy-benzylalcohol, (1R,2R)-1-(m-hydroxyphenyl)-2-amino-1-propanol, (1R,2R)-1-(p-hydroxyphenyl)-2-amino-1-propanol, (1R,2R)-1-phenyl-2-ethylamino-1-propanol, (1R,2R)-1-phenyl-2-amino-1-butanol and (1R,2R)-1-phenyl-2-methylamino-1-butanol.

Additionally, the obtained (1S,2S)-1-(m-hydroxyphenyl)-2-amino-1-propanol can be inverted to produce (1R,2S)-1-(m-hydroxyphenyl)-2-amino-1-propanol (metaraminol).

Among the microorganisms according to this invention, those to which IFO accession numbers have been designated are described in the "List of Cultures, 10th Edition (1966)" published by Institute for Fermentation (IFO) (non-profit organization) and are available from the IFO. The microorganisms to which IAM accession numbers have been designated are described in the "Catalogue of Strains, 1993" published by Institute of Molecular and Cellular Biosciences, the Cell & Functional Polymer General Center, University of Tokyo and are available from its preservation facilities. Further, *Rhodococcus erythropolis* MAK-34 is a novel microorganism isolated from the nature and has been deposited with National Institute of Bioscience and Human-Technology, National Institute of Advanced Science and Technology, METI locating at 1–3, Higashi 1-Chome, Tsukuba, Ibaraki, JAPAN (postal code: 305–8566) as FERM BP-7451 (the date of original deposit: Feb. 15, 2001).

For the microorganism used in this invention, there can be used any of wild-type strains, mutant strains and recombinant strains derived by the techniques of cell engineering such as cell fusion or by the techniques of genetic engineering such as gene manipulations insofar as it is a microorganism capable of acting on the enantiomeric mixture of a α-aminoketone compound of the general formula (I) and producing the corresponding optically active β-amino alcohol of the general formula (II).

There are no particular limitations to the different conditions in the culturing of the microorganisms, and the methods that are ordinarily used may be carried out, where bacteria, fungi, and yeast are cultured in suitable media, respectively. Normally, there may be used liquid media containing carbon sources, nitrogen sources and other nutrients. Any sources may be used for the carbon source of the medium as long as the microorganisms can utilize them. Specifically, there may be used sugars such as glucose, fructose, sucrose, dextrin, starch, and sorbitol; alcohols such as methanol, ethanol, and glycerol; organic acids such as fumaric acid, citric acid, acetic acid, and propionic acid and their salts; hydrocarbons such as paraffin; and mixtures of the foregoing. Any sources may be used for the nitrogen source of the medium as long as the microorganisms can utilize them. Specifically, there may be used the ammonium salts of inorganic acids such as ammonium chloride, ammonium sulfate, and ammonium phosphate; the ammonium salts of organic acids such as ammonium fumarate and ammonium citrate; the salts of nitric acid such as sodium nitrate and potassium nitrate; nitrogen-containing inorganic or organic compounds such as beef extract, yeast extract, malt extract, and peptone; and mixtures of the foregoing. Nutrition sources may also be added appropriately to the medium, which are used in the normal culturing, including inorganic salts, the salts of minute metals, and vitamins. There may also be added to the medium, a substance for inducing the activity of a microorganism, a buffer substance effective to maintain pH, or the like.

The substances for inducing the activity of a microorganism include an activity inducer having the general formula (III):

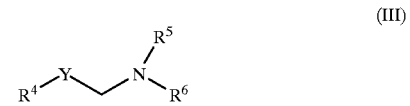

wherein $R^4$ represents lower alkyl; $R^5$ and $R^6$ may be the same or different and each represents a hydrogen atom, lower alkyl, or acyl; Y represents C=O or CH—OH.

The lower alkyl and acyl groups include the ones previously defined respectively. Specifically, the preferred activity inducers include 1-amino-2-propanol, 1-amino-2-hydroxybutane, 1-acetylamino-2-propanol, 1-methylamino-2-propanol, 1-amino-2-oxopropane, 2-amino-3-hydroxybutane, and the like. When asymmetric carbons are present in these compounds, the compounds may be either of optically active forms and racemates, and may appropriately be selected. The addition of these activity inducers to medium induces the activity of microorganisms and the subsequent generation of optically active β-amino alcohols to progress with higher efficiency as compared to the case with no such addition. The activity inducers may be used individually, or may be used as a mixture of plural inducers. The addition levels of such activity inducers are desirably 0.01 to 10 wt. % relative to medium.

Culturing of microorganisms can be carried out under the conditions suited for their growth. Specifically, it can be done at the pH of medium being 3–10, preferably pH 4–9 and at a temperature of 0–50° C., preferably 20–40° C. The culturing of microorganisms can be carried out under aerobatic conditions or anaerobatic conditions. The culturing time is preferably from 10 to 150 hours and should be appropriately determined for the respective microorganisms.

The reaction method in the production of β-amino alcohols according to this invention is not particularly limited insofar as it is a method by which the microorganism acts on the enantiomeric mixture of the α-amino ketone compound having the general formula (I) or a mixture thereof to produce the corresponding optically active β-amino alcohol compound having the general formula (II). The reaction is allowed to start by mixing bacterial cells washed with buffer or water to a aqueous solution of the starting α-aminoketone.

The reaction conditions can be selected from the range within which the generation of the optically active β-amino alcohol compound having the general formula (II) is not impaired. The quantity of bacterial cell is preferably 1/100 to 1000 times, and more preferably 1/10 to 100 times that of racemic aminoketone. The concentration of the racemic aminoketone that is a substrate is preferably from 0.01 to 20%, and more preferably from 0.1 to 10%. Further, the pH of reaction solution is preferably from 5 to 9, and more preferably from 6 to 8; the reaction temperature is preferably from 10 to 50° C., and more preferably from 20 to 40° C. Still further, the reaction time is preferably from 5 to 150 hours and it should be appropriately determined for the respective microorganisms.

In order for the reaction to progress more efficiently, sugars (e.g., glucose), organic acids (e.g., acetic acid), and energy substances (e.g., glycerol) may be added. These may be respectively used alone or may be used as a mixture thereof. The level of addition is preferably 1/100 to 10 times that of substrate. Coenzymes or the like may also be added. Coenzymes such as nicotinamide adenine dinucleotide (NAD), reduced nicotinamide adenine dinucleotide (NADH), nicotinamide adenine dinucleotide phosphate (NADP), and reduced nicotinamide adenine dinucleotide phosphate (NADPH) can be used alone or as a mixture of the foregoing. The level of addition is preferably from 1/1000 to 1/5 times that of the racemic aminoketone. In addition to these coenzymes coenzyme-regenerating enzymes such as glucose dehydrogenase may also be added; and the level of addition is preferably from 1/100 to 10 times that of the racemic aminoketone. Further, sugars (e.g., glucose), organic acids (e.g., acetic acid), and energy substances (e.g., glycerol), coenzymes, coenzyme-regenerating enzymes, and substrates for the coenzyme-regenerating enzymes may respectively be combined for use. These substances are naturally accumulated in bacterial cells, but where their addition as required can increase the reaction rate and yield, they may be appropriately selected.

Furthermore, when a certain salt is added such that the reaction solution may be as described above and the reaction solution is allowed to react under that condition, the racemization of the unreacted α-aminoketone isomer can be accelerated and its conversion to the enantiomer that serves as the substrate for microorganism can be progressed more efficiently. This tends to produce the objective amino alcohol in a high yield of 50% or more from the starting material.

The salts for accelerating the racemization of the unreacted α-aminoketones may be the salts of weak acids such as acetate, tartrate, benzoate, citrate, malonate, phosphate, carbonate, p-nitrophenolate, sulfite, and borate. Preferably, there are used phosphates (e.g., sodium dihydrogenphosphate, potassium dihydrogenphosphate, and ammonium dihydrogenphosphate), carbonates (e.g., sodium carbonate, sodium hydrogencarbonate, potassium carbonate, and ammonium carbonate), citrates (e.g., sodium citrate, potassium citrate, and ammonium citrate), for example. These mixtures may also be used, and desirably, buffers with pH 6.0–8.0 are added to give final concentrations of from 0.01 to 1 M. For example, in the case of a phosphate, sodium dihydrogenphosphate and sodium monohydrogenphosphate are desirably mixed at a ratio of from 9:1 to 5:95.

The optically active α-amino alcohols produced by reaction may be purified by conventional separation/purification means. For example, directly from the reaction solution or after the bacterial cells are separated, optically active β-amino alcohols can be obtained by being subjected to normal purification methods such as membrane separation or extraction with an organic solvent (e.g., toluene and chloroform), column chromatography, concentration at reduced pressure, distillation, recrystallization, and crystallization.

The optical activity of the optically active β-amino alcohol thus produced can be determined by high performance liquid chromatography (HPLC).

EXAMPLES

This invention will be described concretely by way of examples; however, the scope of the invention is not to be limited by these examples.

Preparation Example 1

Preparation of dl-2-methylamino-1-phenyl-1-propanone

Bromine (51.6 ml) was added dropwise to a mixture of 1-phenyl-1-propanone (134 g), sodium carbonate (42 g) and water (200 ml), and reaction was allowed to take place at 70° C. for 3 hours to give a reaction mixture. To the reaction mixture was added 40% aqueous monomethylamine solution (350 ml). After allowing to react at 40° C. for 1 hour, the reaction product was extracted into chloroform (1 l). The reaction product in the chloroform layer was then extracted with dilute hydrochloric acid (100 ml), and activated carbon (3 g) was added to the aqueous layer and filtrated. The filtrate was concentrated to give dl-2-methylamino-1-phenyl-1-propanone hydrochloride (89 g).

Example 1

Production of d-(1S,2S)-pseudoephedrine

*Microbacterium arborescens* IFO 3750 was inoculated to a medium (5 ml) containing 1% glucose, 0.5% peptone, and 0.3% yeast extract, and shake-culturing was carried out at 30° C. for 48 hours. After the cultured solution was centrifuged to give bacterial cells, the cells were placed into a test tube. To this was added 0.1 M sodium phosphate buffer (pH 7.0, 1 ml) and suspended. To this was added dl-2-methylamino-1-phenyl-1-propanone hydrochloride (1 mg) and reaction was allowed to take place under shaking at 30° C. for 24 hours. After the reaction, the reaction solution was centrifuged to remove the bacterial cells and the supernatant was subjected to HPLC to give optically active pseudoephedrine: μ Bondapakphenyl manufactured by Waters Inc.; diameter of 4 mm; length of 300 mm; eluent-0.05 M sodium phosphate buffer (containing 7% acetonitrile); pH 5.0; flow rate of 0.8 ml/min; and detection light wavelength at 220 nm.

The absolute configuration and optical purity were determined with HPLC (Column Sumichiral AGP manufactured by Sumika Chemical Analysis Service; diameter of 4 mm; length of 150 mm; 0.03 M sodium phosphate buffer; pH 7.0; flow rate of 0.5 ml/min; and detection light wavelength at 220 nm). Consequently, only d-pseudoephedrine was obtained selectively, as shown in Table 1.

The produced amounts will be all shown in terms of the amounts of converted hydrochloride hereafter.

Examples 2 to 12

Production of d-(1S,2S)-pseudoephedrine

Except that the microorganisms shown in Table 1 were used in place of *Microbacterium arborescens* IFO 3750, optically active pseudoephedrine was obtained similarly to Example 1. Consequently, only d-pseudoephedrine was obtained selectively, as shown in Table 1.

TABLE 1

| Example | Microorganism | | Optical activity (%) | | | | Produced amount |
|---|---|---|---|---|---|---|---|
| No. | genus | IFO | d-ephedrine | l-ephedrine | d-pseudo ephedrine | l-pseudo ephedrine | (mg/mL) |
| Example 1 | Microbacterium arborescens | 3750 | 0 | 0 | 100 | 0 | 0.16 |
| Example 2 | Klebsiella pneumoniae | 3319 | 0 | 0 | 100 | 0 | 0.3 |
| Example 3 | Aureobacterium esteraromaticum | 3751 | 0 | 0 | 100 | 0 | 0.14 |
| Example 4 | Xanthomonas sp. | 3084 | 0 | 0 | 100 | 0 | 0.049 |
| Example 5 | Pseudomonas putida | 14796 | 0 | 0 | 100 | 0 | 0.1 |
| Example 6 | Mycobacterium smegmatis | IAM 12065 | 0 | 0 | 100 | 0 | 0.24 |
| Example 7 | Mycobacterum diernhoferi | 14797 | 0 | 0 | 100 | 0 | 0.25 |
| Example 8 | Mycobacterum vaccae | 14118 | 0 | 0 | 100 | 0 | 0.28 |
| Example 9 | Mortierella isabellina | 8308 | 0 | 0 | 100 | 0 | 0.15 |
| Example 10 | Cyllindrocarpon sclerotigenum | 31855 | 0 | 0 | 100 | 0 | 0.09 |
| Example 11 | Sporidiobolus johnsonii | 6903 | 0 | 0 | 100 | 0 | 0.07 |
| Example 12 | Rhodococcus erythropolis | MAK-34 | 0 | 0 | 100 | 0 | 0.3 |

Examples 13 to 37

Production of d-(1S,2S)-pseudoephedrine

Except that the microorganisms shown in Table 2 were used in place of *Microbacterium arborescens* IFO 3750, optically active pseudoephedrine was obtained similarly to Example 1. The produced amounts and optical purities of pseudoephedrine are shown In Table 2.

TABLE 2

| Example No. | Microorganism | | produced amount | optical purity (%) |
|---|---|---|---|---|
| | genus | IFO | (mg/ml) | d-pseudoephedrine |
| Example 13 | Nocardioides simplex | 12069 | 0.35 | 99 |
| Example 14 | Mycobacterium phlei | 13160 | 0.27 | 95.6 |
| Example 15 | Mucor ambiguus | 6742 | 0.07 | 93 |
| Example 16 | Mucor javanicus | 4570 | 0.04 | 95 |
| Example 17 | Mucor fragilis | 6449 | 0.17 | 90 |
| Example 18 | Absidia lichtheimi | 4009 | 0.04 | 93 |
| Example 19 | Aspergillus awamori | 4033 | 0.18 | 93 |
| Example 20 | Aspergillus niger | 4416 | 0.11 | 90 |
| Example 21 | Aspergillus oryzae | 4177 | 0.18 | 91 |
| Example 22 | Aspergillus candidus | 5468 | 0.07 | 94 |
| Example 23 | Aspergillus oryzae | IAM2630 | 0.08 | 92 |
| Example 24 | Aspergillus oryzae var. oryzae | 6215 | 0.05 | 95 |
| Example 25 | Penicillium oxalicum | 5748 | 0.06 | 94 |
| Example 26 | Grifola frondosa | 30522 | 0.08 | 92 |
| Example 27 | Eurotium repens | 4884 | 0.08 | 92 |
| Example 28 | Ganoderma lucidum | 8346 | 0.05 | 92.2 |
| Example 29 | Hypocrea gelatinosa | 9165 | 0.27 | 92.2 |
| Example 30 | Helicostylum | 8091 | 0.27 | 93.2 |

TABLE 2-continued

| Example No. | Microorganism genus | IFO | produced amount (mg/ml) | optical purity (%) d-pseudoephedrine |
|---|---|---|---|---|
| | nigricans | | | |
| Example 31 | Aspergillus foetidus var. acidus | 4121 | 0.43 | 91.9 |
| Example 32 | Verticillium fungicola var. fungicola | 6624 | 0.10 | 92.7 |
| Example 33 | Fusarium roseum | 7189 | 0.40 | 89.6 |
| Example 34 | Tritirachium oryzae | 7544 | 0.34 | 92 |
| Example 35 | Armillariella mellea | 31616 | 0.28 | 91 |
| Example 36 | Sporobolomyces salmonicolor | 1038 | 0.14 | 95 |
| Example 37 | Sporobolomyces coralliformis | 1032 | 0.2 | 95 |

Example 38
Production of d-(1S,2S)-pseudoephedrine

Morganella morganii IFO 3848 was inoculated to a medium containing 1% glucose, 0.5% peptone, and 0.3% yeast extract, and shake-culturing was aerobically carried out at 30° C. for 48 hours. After this cultured solution (5 ml) was centrifuged to give bacterial cells, the cells were dried in the air and the resulting dried bacterial cells were suspended in 1 ml of 0.05 M Tris hydrochloric acid buffer (pH 7.5). To the aforementioned dried bacterial cell suspension were added glucose (50 mg), glucose dehydrogenase (0.2 mg), NADP (0.6 mg), NAD (0.6 mg), and dl-2-methylamino-1-phenyl-1-propanone hydrochloride (10 mg) and reciprocation-shaking was carried out at 28° C. and at 300 rpm. After allowing to react for 48 hours, the reaction solution was measured for the produced amount and the optical activity of pseudoephedrine by HPLC similarly to Example 1. Consequently, only d-pseudoephedrine was obtained selectively, as shown in Table 3.

was added, and then concentration to dryness yielded a hydrochloride salt. The hydrochloride salt was dissolved by addition of ethanol and further addition of ether crystallized the reaction product. Consequently, d-pseudoephedrine hydrochloride was obtained. The resulting d-pseudoephedrine crystals (0.32 g) were analyzed on HPLC (Column Sumichiral AGP manufactured by Sumika Chemical Analysis Service; diameter of 4 mm; length of 150 mm; 0.03 M sodium phosphate buffer; pH 7.0; flow rate of 0.5 ml/min; detection light wavelength at UV 220 nm) and the optical activity was found to be 100%.

Example 40

Production of d-(1S,2S)-methylpseudoephedrine

Mycobacterium smegmatis IAM-12065 was inoculated to a medium containing 1% glucose, 0.5% peptone, and 0.3% yeast extract, and shake-culturing was aerobically carried

TABLE 3

| | | | Optical purity (%) | | | | Produced |
|---|---|---|---|---|---|---|---|
| Example No. | Microorganism Genus | IFO | d-ephedrine | l-ephedrine | d-pseudo-ephedrine | l-pseudo-ephedrine | amount (mg/ml) |
| Example 38 | Morganella morganii | 3848 | 0 | 0 | 100 | 0 | 0.79 |

Example 39
Production of d-(1S,2S)-pseudoephedrine hydrochloride

Mycobacterium smegmatis IAM-12065 was inoculated to a medium containing 1% glucose, 0.5% peptone, and 0.3% yeast extract, and shake-culturing was aerobically carried out at 30° C. for 48 hours. After the cultured solution (1 l) was centrifuged to give bacterial cells, the cells was suspended in 50 ml of water, and after addition of dl-2-methylamino-1-phenyl-1-propanone hydrochloride (0.5 g), reciprocation-shaking was carried out at 30° C. and at 150 rpm. One hundred hours after the start of shaking, 7.0 g/l of d-pseudoephedrine was produced in the reaction solution. After the reaction solution was centrifuged to remove the bacterial cells, the pH was adjusted to 12 or greater by addition of sodium hydroxide. Methylene chloride (100 ml) was added to this reaction solution and the reaction product was extracted. The solvent was removed, hydrochloric acid out at 30° C. for 48 hours. The cultured solution (1 l) was filtrated to give bacterial cells, the resulting cells were washed with water, and water was added to form 50 ml of suspension. To the suspension was added 100 mg of 2-dimethylamino-1-phenyl-1-propanone hydrochloride (2 g/l), and reciprocation-shaking was carried out at 30° C. and at 150 rpm for 48 hours. When the reaction solution was analyzed on HPLC (Column Sumichiral AGP manufactured by Sumika Chemical Analytical Center; diameter of 4 mm; length of 150 mm; 0.03 M sodium phosphate buffer; pH 7.0; flow rate of 0.5 ml/min; detection light wavelength at UV 220 nm), it was found that d-(1S,2S)-methylpseudoephedrine was produced at 0.23 g/l and its optical activity was 77%.

Example 41
Production of l-(1R,2R)-pseudoephedrine

*Amycolatopsis alba* IFO 15602 was inoculated to a medium containing 1% glucose, 0.5% peptone and 0.3% yeast extract, and shake-culturing was aerobically carried out at 30° C. for 48 hours. The cultured solution (5 ml) was centrifuged to give bacterial cells. After the cells were suspended in 1 ml of 0.1 M sodium phosphate (pH 7.0) and dl-2-methylamino-1-phenyl-1-propanone hydrochloride (1 mg) was added thereto, reaction was allowed to take place by carrying out reciprocation-shaking at 30° C. and at 150 rpm for 48 hours. When the reaction solution was analyzed on HPLC (Column Sumichiral AGP manufactured by Sumitomo Chemical Analytical Center Co. Ltd.; diameter of 4 mm; length of 150 mm; 0.03 M sodium phosphate buffer; pH 7.0; flow rate of 0.5 ml/min; detection light wavelength at UV 220 nm), it was found that 1-pseudoephedrine was produced selectively. The result is shown in Table 4.

Examples 42 to 46
Production of l-(1R,2R)-pseudoephedrine

Except that the microorganisms shown in Table 4 were used in place of *Amycolatopsis alba* IFO 15602, optically active pseudoephedrine was obtained similarly to Example 41. Consequently, only l-pseudoephedrine was obtained selectively, as shown in Table 4.

Example 49
Production of l-(1R,2R)-pseudoephedrine

*Coprinus rhizophorus* IFO 30197 was inoculated to a medium containing 1% glucose, 0.5% peptone and 0.3% yeast extract, and culturing was aerobically carried out at 30° C. for 48 hours. After this cultured solution (5 ml) was centrifuged to give bacterial cells, the cells were dried in the air and the resulting dried bacterial cells were suspended in 1 ml of 0.05 M Tris hydrochloric acid buffer (pH 7.5). To this were added glucose (50 mg), glucose dehydrogenase (0.2 mg), NADP (0.6 mg), NAD (0.6 mg) and dl-2-methylamino-1-phenyl-1-propanone hydrochloride (10 mg). Reaction was allowed to take place by carrying out reciprocation-shaking at 28° C. and at 300 rpm for 48 hours. The reaction solution was analyzed on HPLC (Column Sumichiral AGP manufactured by Sumika Chemical Analysis Service; diameter of 4 mm; length of 150 mm; 0.03 M sodium phosphate buffer; pH 7.0; flow rate of 0.5 ml/min; detection wavelength at UV 220 nm). The produced amounts and the optical activities of pseudoephedrine were determined. Consequently, only l-pseudoephedrine was obtained selectively, as shown in Table 6.

TABLE 4

| | Microorganism | | Optical activity (%) | | | | Produced amount |
|---|---|---|---|---|---|---|---|
| Example No. | genus | IFO | d-ephedrine | l-ephedrine | d-pseudo ephedrine | l-pseudo ephedrine | (mg/ml) |
| Example 41 | *Amycolatopsis alba* | 15602 | 0 | 0 | 0 | 100 | 0.33 |
| Example 42 | *Amycolatopsis azurea* | 14573 | 0 | 0 | 0 | 100 | 0.064 |
| Example 43 | *Amycolatopsis coloradensis* | 15804 | 0 | 0 | 0 | 100 | 0.5 |
| Example 44 | *Amycolatopsis orientalis lurida* | 14500 | 0 | 0 | 0 | 100 | 0.18 |
| Example 45 | *Amycolatopsis orientalis orientalis* | 12360 | 0 | 0 | 0 | 100 | 0.5 |
| Example 46 | *Serratia marcescens* | 3736 | 0 | 0 | 0 | 100 | 0.47 |

Examples 47 and 48
Production of l-(1R,2R)-pseudoephedrine

Except that the microorganisms shown in Table 5 were used in place of *Amycolatopsis alba* IFO 15602, optically active pseudoephedrine was obtained similarly to Example 41. The produced amounts and optical purities of 1-pseudoephedrine are shown in Table 5.

TABLE 5

| | Microorganism | | Optical purity (%) | Produced amount |
|---|---|---|---|---|
| Example No. | genus | IFO | 1-pseudoephedrine | (mg/ml) |
| Example 47 | *Rhodococcus erythropolis* | 12540 | 98.6 | 0.11 |
| Example 48 | *Rhodococcus rhodochrous* | 15564 | 96.6 | 0.10 |

TABLE 6

| Example No. | Microorganism genus | IFO | Optical purity (%) | | | | Produced amount (mg/ml) |
| | | | d-ephedrine | l-ephedrine | d-pseudo-ephedrine | l-pseudo-ephedrine | |
|---|---|---|---|---|---|---|---|
| Example 49 | Corprinus rhizophorus | 30197 | 0 | 0 | 0 | 100 | 1.09 |

Example 50
Production of (1S,2S)-1-(p-hydroxyphenyl)-2-methylamino-1-propanol

Rhodococcus erythropolis MAK-34 strain was shake-cultured in a medium (5 ml) containing 1% saccharose, 0.5% corn steep liquor, 0.1% potassium dihydrogenphosphate, 0.3% dipotassium hydrogenphosphate and 0.1% 1-amino-2-propanol at 30° C. for 48 hours. Either centrifugation or filtration yielded bacterial cells. To this were added an adequate amount of water, 1M phosphate buffer (0.2 ml; pH 7.0), glucose (10 mg) and racemic 1-(p-hydroxyphenyl)-2-methylamino-1-propanol hydrochloride (1 mg), and they were mixed. One milliliter was shaken for reaction at 30° C. for 48 hours. The reaction solution was either centrifuged or filtered. The supernatant was analyzed on HPLC ($\mu$ Bondapakphenyl manufactured by Waters Inc.; diameter of 4 mm; length of 300 mm; eluent—0.05 M sodium phosphate buffer (containing 7% acetonitrile); pH 6.5; flow rate of 0.8 ml/min; detection wavelength at UV 220 nm). Consequently, it was confirmed that threo-1-(p-hydroxyphenyl)-2-methylamino-1-propanol hydrochloride was produced at 0.6 mg/ml. To determine the optical purity of the product, the sample was analyzed on HPLC (Sumichiral OA-4900 manufactured by Sumika Chemical Analysis Service; eluent:hexane:dichloroethane:methanol: trifluoroacetic acid=240:140:40:1; flow rate of 1 ml/min; detection wavelength at UV 254 nm). Consequently, it was found that (1S,2S)-1-(p-hydroxyphenyl)-2-methylamino-1-propanol was obtained in 100% optical purity.

Examples 51 to 54
Production of optically active 1(p-hydroxyphenyl)-2-methylamino-1-propanol Except that the microorganisms shown in Table 7 were used in place of Rhodococcus erythropolis MAK-34 strain and the culturing conditions in the table were followed, reaction was carried out similarly to Example 50 and optically active 1-(p-hydroxyphenyl)-2-methylamino-1-propanol was obtained. The results are shown in Table 7. In all instances, the optically active compound was obtained efficiently.

The culture conditions listed in Tables 7–9 are as follows:

Culture conditions 1: A microorganism was inoculated to a medium (20 ml) containing 1% glucose, 0.5% peptone, 10 and 0.3% yeast extract (pH7.0) and culturing was carried out at 30° C. for 48 hours under the shaking condition of 150 rpm.

Culture conditions 2: A microorganism was inoculated to a medium (20 ml, pH 6.0) containing 5% malt extract and 0.3% yeast extract and culturing was carried out at 30° C. for 48 hours under the shaking condition of 150 rpm.

TABLE 7

| Example No. | Strain | IFO | Culture conditions | Produced amount (mg/mL) | Stereochemical configuration of product | Optical purity (%) |
|---|---|---|---|---|---|---|
| Example 51 | Helicostylum nigricans | 8091 | 1 | 0.06 | 1S 2S | 90 |
| Example 52 | Amycolatopsis orientalis lurida | 14500 | 1 | 0.01 | 1R 2R | 100 |
| Example 53 | Amycolatopsis orientalis orientalis | 12362 | 1 | 0.02 | 1R 2R | 100 |
| Example 54 | Amycolatopsis orientalis orientalis | 12806 | 1 | 0.01 | 1R 2R | 100 |

Example 55
Production of (1S,2S)-2-ethylamino-1-phenyl-1-propanol

Rhodococcus erythropolis MAK-34 strain was shake-cultured in a medium (5 ml) containing 1% saccharose, 0.5% corn steep liquor, 0.5% potassium dihydrogenphosphate, 0.3% dipotassium hydrogenphosphate and 0.1% 1-amino-2-propanol at 30° C. for 48 hours. Either centrifugation or filtration yielded bacterial cells. To this were added an adequate amount of water, 1M phosphate buffer (0.2 ml, pH 7.0), glucose (10 mg) and racemic 2-ethylamino-1-phenyl-1-propanone hydrochloride (1 mg), and they were mixed. One milliliter was shaken for reaction at 30° C. for 48 hours. The reaction solution was either centrifuged or filtered. The supernatant was analyzed on HPLC ($\mu$ Bondaspherephenyl manufactured by Waters Inc.; diameter of 4 mm; length of 150 mm; eluent—0.05 M sodium phosphate buffer (containing 7% acetonitrile); pH 6.5; flow rate of 0.8 ml/min; detection wavelength at UV 220 nm). Consequently, it was confirmed that threo-2-ethylamino-1-phenyl-1-propanol hydrochloride was produced at 0.47 mg/ml. To determine the optical purity of the product, the sample was analyzed on HPLC (Column OD manufactured by Daicel Chemical Industries Ltd.; diameter of 4.6 mm; length of 250 mm; eluent-hexane:isopropanol:diethylamine=90:10:0.1; flow rate of 1 ml/min; detection wavelength at UV 254 nm). Consequently, the product was found to be (1S,2S)-2-ethylamino-1-phenyl-1-propanol (optical purity: 100%).

Examples 56 to 58

Production of (1R,2R)-2-ethylamino-1-phenyl-1-propanol

Except that the microorganisms shown in Table 8 were used in place of Rhodococcus erythropolis MAK-34 strain and the culturing conditions in the table were followed, reaction was carried out similarly to Example 55 and (1R,2R)-2-ethylamino-1-phenyl-1-propanol was obtained. The results are shown in Table 8.

glucose (10 mg), and racemic 1-(m-hydroxyphenyl)-2-amino-1-propanone hydrochloride (1 mg), and they were mixed. One milliliter was shaken for reaction at 30° C. for 48 hours. This was either centrifuged or filtered. The supernatant was analyzed on HPLC ($\mu$ Bondapakphenyl manufactured by Waters Inc.; diameter of 4 mm; length of 300 mm; eluent—0.05 M sodium phosphate buffer (containing 7% acetonitrile); pH 6.5; flow rate of 0.8 ml/min; detection wavelength at UV 220 nm). Consequently, it was confirmed that threo-1-(m-hydroxyphenyl)-2-amino-1-propanol was produced. To determine the optical purity of the product, the sample was analyzed on HPLC (Crownpak CR+ manufactured by Daicel Chemical Industries Ltd.; perchloric acid, pH 2.0, 1.0 ml/min, UV 254 nm). Consequently, it was found that optical active 1-(m-hydroxyphenyl)-2-amino-1-propanol with its stereochemical configuration shown in Table 9.

TABLE 8

| Example No. | Strain | IFO | Culture conditions | Produced amount (mg/mL) | Stereochemical configuration of product | Optical purity (%) |
|---|---|---|---|---|---|---|
| Example 56 | Amycolatopsis alba | 15602 | 1 | 0.01 | 1R 2R | 100 |
| Example 57 | Amycolatopsis orientalis orientalis | 12806 | 1 | 0.01 | 1R 2R | 100 |
| Example 58 | Rhodotorula aurantiaca | 0951 | 2 | 0.01 | 1R 2R | 100 |

TABLE 9

| Example No. | Strain | IFO | Culture conditions | Produced amount (mg/mL) | Stereochemical configuration of product | Optical purity (%) |
|---|---|---|---|---|---|---|
| Example 59 | Helicostylums nigricans | 8091 | 1 | 0.01 | 1S 2S | 100 |
| Example 60 | Amycolatopsis albas | 15602 | 1 | 0.01 | 1R 2R | 78 |
| Example 61 | Rhodotorula aurantiaca | 0951 | 2 | 0.01 | 1R 2R | 100 |

Examples 59 to 61

Production of Optically Active 1-(m-hydroxyphenyl)-2-amino-1-propanol

The microorganisms listed in Table 9 were shake-cultured in a medium (5 ml) at 30° C. for 48 hours under their respective conditions. Either centrifugation or filtration yielded bacterial cells. To this were added an adequate amount of water, 1M phosphate buffer (0.2 ml, pH 7.0), Example 62

Production of (1R,2R)-1-(p-hydroxyphenyl)-2-amino-1-propanol

*Amycolatopsis alba* IFO-15602 was cultured under culture conditions 1, and either centrifugation or filtration yielded bacterial cells. To these were added an adequate amount of water, 1M phosphate buffer (0.2 ml, pH 7.0), glucose (10 mg) and racemic 1-(p-hydroxyphenyl)-2-amino-1-propanone hydrochloride (1 mg), and they were mixed. One milliliter was shaken for reaction at 30° C. for 48 hours. This was either centrifuged or filtered. The supernatant was analyzed on HPLC ($\mu$ Bondapakphenyl manufactured by Waters Inc.; diameter of 4 mm; length of 300 mm; eluent-0.05 M sodium phosphate buffer (containing 7% acetonitrile); pH 6.5; flow rate of 0.8 ml/min; detection wavelength at UV 220 nm). Consequently, it was confirmed that threo-1-(p-hydroxyphenyl)-2-amino-1-propanol hydrochloride was produced at 0.03 mg/ml. To determine the optical purity of the product, the sample was analyzed on HPLC (Crownpak CR+ manufactured by Daicel Chemical Industries Ltd.; perchloric acid, pH 2.0, 1.0 ml/min, UV 254 nm). Consequently, the product was found to be (1R,2R)-1-(p-hydroxyphenyl)-2-amino-1-propanol (optical purity: 82%).

Example 63
Production of (1S,2S)-1-phenyl-2-amino-1-butanol

*Helicostylum nigricans* IFO-8091 was cultured under culture conditions 1. Either centrifugation or filtration yielded bacterial cells. To these were added an adequate amount of water, 1M phosphate buffer (0.2 ml, pH 7.0), glucose (10 mg) and racemic 1-phenyl-2-amino-1-butanone hydrochloride (1 mg), and they were mixed. One milliliter was shaken for reaction at 30° C. for 48 hours. The reaction solution was either centrifuged or filtered. The supernatant was analyzed on HPLC ($\mu$ Bondaspherephenyl manufactured by Waters Inc.; diameter of 4 mm; length of 150 mm; eluent-0.05 M sodium phosphate buffer (containing 7% acetonitrile); pH 6.5; flow rate of 0.8 ml/min; detection wavelength at UV 220 nm). Consequently, it was found that threo-1-phenyl-2-amino-1-butanol hydrochloride was produced at 0.62 mg/ml. To determine the optical purity of product, the sample was analyzed on HPLC (OD by Daicel Chemical Industries Ltd.; diameter of 4.6 mm; length of 250 mm; hexane:isopropanol:diethylamine=90:10:0.1; 1 ml/min; UV 254 nm). Consequently, the product was found to be (1S,2S)-1-phenyl-2-amino-1-butanol.

Example 64
Production of (1R,2R)-1-phenyl-2-amino-1butanol

*Amycolatopsis orientalis* IFO-12806 was cultured under culture conditions 1, and similarly to Example 63, (1R,2R)-1-phenyl-2-amino-1-butanol could be produced at 0.21 mg/ml.

Example 65
The Effect of Addition of Inducer (1)

1-Amino-2-hydroxypropanone was added to medium 1 (Table 10) so that a level of 5 g/L could be obtained. Five milliliters was then poured into a test tube. With a silicone stopper it was sterilized in an autoclave at 121° C. for 30 minutes. The microorganisms listed in Table 11 were inoculated to this medium and to the medium with no addition of the inducer, respectively; and they were shake-cultured at 300 rpm and at 30° C. for 48 hours. The culture (0.5 mL) was centrifuged at 10,000 G for 20 minutes. The bacterial cells obtained by removal of the supernatant were suspended by addition of water to prepare a uniform suspension. To this were added water, buffer and dl-2-methylamino-1-phenyl-1-propanone hydrochloride (10 mg), forming 1 mL. The one milliliter was poured into a test tube and reaction was allowed to take place under shaking at 150 rpm and at 30° C. for 12 hours. After the reaction, the bacterial cells were removed by centrifugation and the supernatant was subjected to HPLC, whereby the produced amount of pseudoephedrine was determined (HPLC conditions: $\mu$ Bondapakphenyl manufactured by Waters Inc.; diameter of 4 mm; length of 300 mm; eluent—0.05 M sodium phosphate buffer (containing 7% acetonitrile); pH 6.5; flow rate of 0.8 ml/min; detection wavelength at UV 220 nm).

As the results are shown in Table 11, the produced amounts of pseudoephedrine when culturing was carried out with the addition of the inducer displayed remarkable increases as compared to the culturing with no addition of inducer.

TABLE 10

| Composition of medium 1 | Composition of medium 2 | Composition of medium 3 | Composition of medium 4 |
|---|---|---|---|
| saccharose 1% | glucose 0.1% | glucose 1% | soluble starch 1% |
| corn steep liquor 0.5% | tryptone 0.5% | Bactopeptone 0.5% | glucose 0.5% |
| potassium dihydrogen-phosphate 0.1% | yeast extract 0.5% | yeast extract 0.3% | Nzaminetype A 0.3% |
| dipotassium hydrogen-phosphate 0.3% | dipotassium hydrogen-phosphate pH 7.0 | pH 7.0 | tryptone 0.5% |
| p-aminobenzoic acid 0.01% | | | yeast extract 0.2% |
| H 7.0 | | | dipotassium hydrogen-phosphate 0.1% |
| | | | magnesium sulfate 7H$_2$O 0.05% |

TABLE 11

| No. | Microorganism | No. | Medium | Produced amount (no addition) mg | Produced amount (addition) mg |
|---|---|---|---|---|---|
| 1 | *Rhodococcus erythropolis* | MAK-34 | 1 | 0.018 | 1.26 |
| 2 | *Mycobacterium chlorophenolicum* | IFO-15527 | 3 | 0.032 | 0.77 |
| 3 | *Mycobacterium smegmatis* | IFO-12065 | 3 | 0.048 | 0.21 |
| 4 | *Nocardioides simplex* | IFO-12069 | 2 | 0 | 0.19 |
| 5 | *Klebsiella pneumoniae* | IFO-3319 | 2 | 0.018 | 0.066 |
| 6 | *Absidia lichtheimi* | IFO-4409 | 4 | 0.0035 | 0.22 |
| 7 | *Aspergillus awamori* | IFO-4033 | 4 | 0.00048 | 1.17 |
| 8 | *Aspergillus candidus* | IFO-5468 | 4 | 0.0092 | 0.018 |
| 9 | *Penicillium cyaneum* | IFO-5337 | 4 | 0.031 | 1.26 |
| 10 | *Hypocrea gelatinosa* | IFO-9165 | 4 | 0.0058 | 0.64 |
| 11 | *Helicostylum nigricans* | IFO-8091 | 4 | 0.0067 | 0.52 |
| 12 | *Tritirachium oryzae* | IFO-7544 | 4 | 0.0047 | 0.078 |
| 13 | *Armillariella mellea* | IFO-31616 | 4 | 0.0042 | 0.46 |

Example 66
The Effect of Addition of Inducers (2)

*Rhodococcus erythropolis* MAK-34 was inoculated to 5 ml of a medium (pH 7.0) containing 1.0% saccharose, 0.5% corn steep liquor, 0.1% dipotassium hydrogenphosphate, 0.3% potassium dihydrogenphosphate, 0.01% p-aminobenzoic acid and each inducer; and shake-culturing was carried out at 30° C. for 48 hours. After the culture was centrifuged to give bacterial cells, they were placed into a test tube and suspended by adding 1.0 ml of 0.2 M sodium phosphate buffer (pH 7.0) thereto. To this were added dl-2-methylamino-1-phenyl-1-propanone hydrochloride (10 mg) and glucose (20 mg) and reaction was allowed to take place under shaking at 30° C. for 16 hours. After the reaction, the reaction solution was centrifuged to remove bacterial cells, and the supernatant was subjected to HPLC, producing optically active pseudoephedrine (μ Bondaspherephenyl manufactured by Waters Inc.; diameter of 4 mm; length of 150 mm; eluent—7% acetonitrile-0.05 M sodium phosphate buffer (pH 6.5); flow rate of 0.8 ml/min; detection wavelength at 220 nm). As shown in Table 12, the production displayed remarkably higher values than does the case without the addition of inducer.

TABLE 12

| Compound name | Produced amount (mg) |
| --- | --- |
| 1-acetylamino-2-propanol | 3.00 |
| 1-methylamino-2-propanol | 2.83 |
| 1-amino-2-oxopropane | 1.97 |
| 2-amino-3-hydroxybutane | 0.05 |
| 1-amino-2-hydroxybutane | 0.65 |
| no addition | 0.02 |

Comparative Example 1

Except that *Brettanomyces anomalus* IFO 0642 was used instead of *Microbacterium arborescens* IFO 3750, the production reaction of pseudoephedrine was attempted similarly to Example 1. However, no reduced product was obtained.

Comparative Example 2

Except that *Candida guilliermondii* IFO 0566 was used instead of *Microbacterium arborescens* IFO 3750, the production reaction of pseudoephedrine was attempted similarly to Example 1. However, no reduced product was obtained.

Comparative Example 3

Except that *Schizosaccharomyces pombe* IFO 0358 was used instead of *Microbacterium arborescens* IFO 3750, the production reaction of pseudoephedrine was attempted similarly to Example 1. However, no reduced product was obtained.

Comparative Example 4

Except that *Bacillus subtilis* IFO 3037 was used instead of *Microbacterium arborescens* IFO 3750, the production reaction of pseudoephedrine was attempted similarly to Example 1. However, no reduced product was obtained.

Industrial Applicability

As described above, the process for producing an optically active β-amino alcohol according to this invention allows the β-amino alcohol having the desired optical activity to be produced from an enantiomeric mixture of an α-aminoketone compound or a salt thereof in a high yield as well as in a highly selective manner with a simple process while sufficiently preventing the generation of diastereomeric byproducts.

Accordingly, this invention will make it possible to produce pseudoephedrines, among others, having the desired optical activity in a high yield as well as in a highly selective manner and thus it is valuable in the manufacture of drugs and their intermediates.

What is claimed is:

1. A process for producing an optical active β-amino alcohol, the process comprising allowing at least one microorganism selected from the group consisting of microorganisms belonging to the genus *Morganella* genus, the genus *Microbacterium*, the genus *Sphingobacterium*, the genus *Nocardioides*, the genus *Mucor*, the genus *Absidia*, the genus *Aspergillus*, the genus *Penicillium*, the genus *Grifola*, the genus *Eurotium*, the genus *Ganoderma*, the genus *Hypocrea*, the genus *Helicostylum*, the genus *Verticillium*, the genus *Fusarium*, the genus *Tritirachium*, the genus *Mortierella*, the genus *Armillariella*, the genus *Cylindrocarpon*, the genus *Klebsiella*, the genus *Aureobacterium*, the genus *Xanthomonas*, the genus *Pseudomonas*, the genus *Mycobacterium*, the genus *Sporobolomyces*, the genus *Sporidiobolus*, the genus *Amycolatopsis*, the genus *Coprinus*, the genus *Serratia*, the genus *Rhodococuss* and the genus *Rhodotorula* to act on an enantiomeric mixture of an α-amino ketone or a salt thereof having the general formula (I):

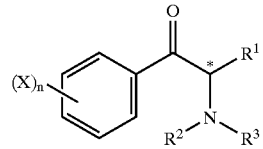

(I)

wherein X may be the same or different and represents at least one member selected from the group consisting of a halogen atom, lower alkyl, hydroxyl optionally protected with a protecting group, nitro and sulfonyl; n represents an integer of from 0 to 3; $R^1$ represents lower alkyl; $R^2$ and $R^3$ may be the same or different and represent at least one member selected from the group consisting of a hydrogen atom and lower alkyl; and "*" represents an asymmetric carbon, to produce an optically active β-amino alcohol compound with the desired optical activity having the general formula (II):

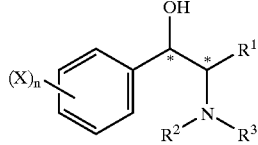

(II)

wherein X, n, $R^1$, $R^2$, $R^3$ and "*" are as previously defined.

2. The process for producing an optically active β-amino alcohol according to claim 1, wherein the microorganism is at least one microorganism selected from the group consisting of microorganisms belonging to *Morganella morganii*, *Microbacterium arborescens*, *Sphingobacterium multivorum*, *Nocardioides simplex*, *Mucor ambiguus*, *Mucor javanicus*, *Mucor fragilis*, *Absidia lichtheimi*, *Aspergillus awamori*, *Aspergillus niger*, *Aspergillus oryzae*, *Aspergillus candidus*, *Aspergillus oryzae* var. *oryzae*, *Aspergillus foetidus* var. *acidus*, *Penicillium oxalicum*, *Grifola frondosa*, *Eurotium repens*, *Ganoderma lucidum*, *Hypocrea gelatinosa*, *Helicostylum nigricans*, *Verticillium fungicola* var. *fungicola*, *Fusarium roseum*, *Tritirachium oryzae*, *Mortierella isabellina*, *Armillariella mellea*, *Cylindrocarpon sclerotigenum*, *Klebsiella pneumoniae*, *Aureobacterium esteraromaticum*, *Xanthomonas* sp., *Pseudomonas putida*, *Mycobacterium smegmatis*, *Mycobacterium diernhoferi*, Mycobacterium vaccae, Mycobacterium phlei, Mycobacterium fortuitum, Mycobacterium chlorophenolicum, Sporobolomyces salmonicolor, Sporobolomyces coralliformis, Sporidiobolus johnsonii, Amycolatopsis alba, Amycolatopsis azurea, Amycolatopsis coloradensis, Amycolatopsis orientalis lurida, Amycolatopsis orientalis orientalis, Coprinus rhizophorus, Serratia marcescens, Rhodococcus erythropolis, Rhodococcus rhodochrous and Rhodotorula aurantiaca.

3. The process for producing an optically active β-amino alcohol according to claim 1, wherein the microorganism is at least one microorganism selected from the group consisting of microorganisms belonging to the genus *Morganella*, the genus *Microbacterium*, the genus *Sphingobacterium*, the genus *Nocardioides*, the genus *Mucor*, the genus *Absidia*, the genus *Aspergillus*, the genus *Penicillium*, the genus *Grifola*, the genus *Eurotium*, the genus *Ganoderma*, the genus *Hypocrea*, the genus *Helicostylum*, the genus *Verticillium*, the genus *Fusarium*, the genus *Tritirachium*, the genus *Mortierella*, the genus *Armillariella*, the genus *Cylindrocarpon*, the genus *Klebsiella*, the genus *Aureobacterium*, the genus *Xanthomonas*, the genus *Pseudomonas*, the genus *Mycobacterium*, the genus *Sporobolomyces*, the genus *Sporidiobolus* and the *Rhodococuss* genus; and the β-amino alcohol having the general formula (II) is (1S,2S)-amino alcohol.

4. The process for producing an optically active β-amino alcohol according to claim 3, wherein the microorganism is at least one microorganism selected from the group consisting of microorganisms belonging to *Morganella morganii, Microbacterium arborescens, Sphingobacterium multivorum, Nocardioides simplex, Mucor ambiguus, Mucor javanicus, Mucor fragilis, Absidia lichtheimi, Aspergillus awamori, Aspergillus niger, Aspergillus oryzae, Aspergillus candidus, Aspergillus oryzae var. oryzae, Aspergillus foetidus var. acidus, Penicillium oxalicum, Grifola frondosa, Eurotium repens, Ganoderma lucidum, Hypocrea gelatinosa, Helicostylum nigricans, Verticillium fungicola var. fungicola, Fusarium roseum, Tritirachium, oryzae, Mortierella isabellina, Armillariella mellea, Cylindrocarpon sclerotigenum, Klebsiella pneumoniae, Aureobacterium esteraromaticum, Xanthomonas sp., Pseudomonas putida, Mycobacterium smegmatis, Mycobacterium diernhoferi, Mycobacterium vaccae, Mycobacterium phlei, Mycobacterium fortuitum, Mycobacterium chlorophenolicum, Sporobolomyces salmonicolor, Sporobolomyces coralliformis, Sporidiobolus johnsonii, Rhodococus erythropolis* and *Rhodococcus rhodochrous*.

5. The process for producing an optically active β-amino alcohol according to claim 1, wherein the microorganism is at least one microorganism selected from the group consisting of microorganisms belonging to the genus *Amycolaptopsis*, the genus *Coprinus*, the genus *Serratia*, the genus *Rhodococuss* and the genus *Rhodotorula*; and the optically active β-amino alcohol having the general formula (II) is (1R,2R)-amino alcohol.

6. The process for producing an optically active β-amino alcohol according to claim 5, wherein the microorganism is at least one microorganism selected from the group consisting of microorganisms belonging to *Amycolatopsis alba, Amycolatopsis azurea, Amycolatopsis coloradensis, Amycolatopsis orientalis lurida, Amycolatopsis orientalis orientalis, Coprinus rhizophorus, Serratia marcescens, Rhodococcus erythropolis, Rhodococcus rhodochrous* and *Rhodotorula aurantiaca*.

7. The process for producing an optically active β-amino alcohol according to any of claims 1–6, wherein the microorganism is cultured in a medium to which there has been added an activity inducer having the general formula (III):

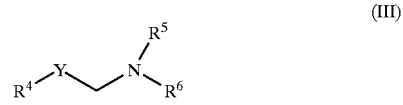
(III)

wherein $R^4$ represents lower alkyl; $R^5$ and $R^6$ may be the same or different and each represents a hydrogen atom, lower alkyl or acyl; and Y represents C=O or CH—OH.

* * * * *